United States Patent
Krawchuk

(10) Patent No.: US 9,179,711 B2
(45) Date of Patent: Nov. 10, 2015

(54) SWADDLING SUIT

(76) Inventor: Hana-Lia Krawchuk, Maroubra (AU)

( * ) Notice: Subject to any disclaimer, the term of this patent is extended or adjusted under 35 U.S.C. 154(b) by 260 days.

(21) Appl. No.: 12/920,034

(22) PCT Filed: Jun. 25, 2010

(86) PCT No.: PCT/AU2010/000800
§ 371 (c)(1),
(2), (4) Date: Aug. 27, 2010

(87) PCT Pub. No.: WO2011/000025
PCT Pub. Date: Jan. 6, 2011

(65) Prior Publication Data
US 2011/0180079 A1   Jul. 28, 2011

(30) Foreign Application Priority Data
Jun. 30, 2009   (AU) ................................ 2009903034

(51) Int. Cl.
*A61F 5/37* (2006.01)
*A41B 13/06* (2006.01)
*A47G 9/08* (2006.01)

(52) U.S. Cl.
CPC ............. *A41B 13/06* (2013.01); *A47G 9/083* (2013.01)

(58) Field of Classification Search
CPC ..... A47D 15/02; A47D 15/005; A47D 11/00; A47D 13/1272; A47B 13/06; A47B 13/08; A47B 13/065
USPC ....... 128/873; 2/69.5, 70, 75, 80, 83
See application file for complete search history.

(56) References Cited

U.S. PATENT DOCUMENTS

| | | | |
|---|---|---|---|
| 2,675,557 A * | 4/1954 | Kempner, Jr. ............... | 2/114 |
| 3,259,126 A * | 7/1966 | Greiert ............... | 128/873 |
| 4,611,353 A | 9/1986 | Als et al. | |
| 5,722,094 A * | 3/1998 | Ruefer ............... | 2/69.5 |
| 7,587,769 B1 | 9/2009 | McDermott | |
| 2003/0131411 A1* | 7/2003 | Gibson ............... | 5/482 |
| 2009/0064390 A1* | 3/2009 | Beiring et al. ............ | 2/80 |
| 2009/0099632 A1* | 4/2009 | Krier ............... | 607/108 |
| 2013/0139290 A1* | 6/2013 | Barski ............... | 2/69.5 |
| 2013/0269080 A1* | 10/2013 | Parker ............... | 2/69.5 |

FOREIGN PATENT DOCUMENTS

| WO | 2007098558 A1 | 9/2007 |
|---|---|---|
| WO | WO 2007098558 A1 * | 9/2007 |

OTHER PUBLICATIONS

Merriam-Webster definition of "Resilient"; www.merriam-webster.com/dictionary/resilient; accessed Jun. 30, 2012.*
"merriamwebster_definition_resilient.pdf".*
ergoPouch, Healthy Sleeping, http://www.ergopouch.com.au/swaddle.html.
Woombie, Swaddle Snuggle Sleep, http://www.thewoombie.com.au.

* cited by examiner

*Primary Examiner* — Alireza Nia
*Assistant Examiner* — Caitlin Carreiro
(74) *Attorney, Agent, or Firm* — Levine Mandelbaum PLLC

(57) ABSTRACT

A new or alternative swaddling suit that swaddles infants by sufficiently restraining movement of the limbs to suppress the startle reflex, yet allowing movement of hand to mouth thereby facilitating non-nutritive sucking and allowing the infant to self-soothe by sucking the hands.

18 Claims, 10 Drawing Sheets

SWADDLING SUIT

TECHNICAL FIELD

The present invention relates to swaddles for infants, and in particular to swaddle garments.

The invention has been developed primarily for use as a means for swaddling infants for safe sleeping. However, it will be appreciated that the invention is not restricted to this particular use.

BACKGROUND

It is now well established that putting an infant to sleep on his or her back is the single most important step in reducing the risk of sudden infant death syndrome (SIDS).

Recent research also suggests that a baby's risk for SIDS can be greatly reduced by using a pacifier. Medical research also shows that babies who can satiate their natural sucking reflex sleep better. Experts recommend giving babies a pacifier every time they are placed to sleep. The exact reason that pacifiers reduce the risk of SIDS is not known. One suggestion is that the presence of a pacifier in the mouth may discourage babies from turning over onto their tummy because turning or moving may dislodge the pacifier. Another suggestion is that pacifier use and/or the sucking reflex helps keep the tongue positioned forward, keeping the airways open. Yet another suggestion is that pacifiers stimulate upper airway muscles and saliva production, so using pacifiers may keep babies from falling into a deep sleep, which is protective against SIDS.

One of the factors that has led to a revival in the ancient practice of swaddling is the practice of putting babies to sleep on their backs as this helps to reduce the incidence of SIDS. However, babies tend to sleep better on their tummies than on their backs. Swaddling has been found to assist infants sleep more comfortably on their backs and to assist in easing colic, which also improves sleep. Swaddling is the practice of wrapping infants tightly in a blanket or cloth so that movement of the limbs is restricted.

Medical research has shown that swaddling and sleeping supine (on the back) promotes more efficient sleep, with fewer spontaneous awakenings compared with sleeping supine but unswaddled. Swaddling seems to inhibit each step from sighs through startles to full arousal in the arousal pathway. This results in swaddled babies sleeping longer and being more likely to return to sleep on their own: Swaddling: a systematic review, Bregje E. van Sleuwen, et al, Pediatrics vol 120, number 4, October 2007.

To achieve the benefits of swaddling, infants need to be wrapped sufficiently tight to restrain the limbs and inhibit the movements associated with a full startle reflex, which can wake babies from sleep. The startle reflex is seen in infants from birth to around 6 months of age (some sources indicate it can occur in infants as old as eight months). The startle reflex is a natural reflex that babies are born with, and can be triggered by loud noise or sudden movement. In response to the trigger, the baby throws back his/her head, extends out the arms and legs, cries, then pulls the arms and legs back in. A baby's own cry can trigger the reflex. It can also be triggered during sleep, causing the baby to wake.

Care needs to be taken not to swaddle too tightly because this can compress the chest and make breathing difficult. There is also an increased risk of overheating especially when the head is covered or when there is infection. Improper swaddling can also lead to a risk of hip dysplasia (including hip dislocation) especially when swaddling with the hips and legs in extension and adduction (i.e. drawn toward the midline or sagittal plane of the body).

Other risks associated with swaddling babies includes an increased risk of SIDS when a swaddled infant is placed prone (on his or her front) or able to turn to prone position. The SIDS risk seems to be increased by swaddling with the head covered. There is also a slightly increased risk of acute respiratory infections, which seems to be related to the tightness of swaddling. These are discussed in the systematic review of swaddling referred to above.

Therefore, to swaddle properly and effectively, and to achieve the desired result, the blanket must be snug enough to immobilise the infant's arms, and to a certain degree its legs, but loose enough that it is still comfortable and not increase the risk of hip dysplasia or suppressed respiration.

Many parents and carers experience difficulty with swaddling due to unfamiliarity with swaddling techniques. If not swaddled correctly, the infant often wriggles free of the swaddle thus becoming exposed to a risk of suffocation or SIDS-related issues due to loose bedding and unrestricted positioning of the infant. However, swaddling alone cannot eliminate these risks. This is especially true for infants that are more than around six weeks old, when they are stronger and more active than newborns. Even when swaddled tightly with all limbs securely enclosed, infants can potentially roll, becoming entrapped in the swaddling blanket or trapped face down while still wrapped in the blanket.

To overcome the difficulty faced by parents and carers in learning proper swaddling techniques and to address the problems of improper swaddling, various swaddling suits have been developed. Swaddling suits such as the infant safety suit of WO 2007/098558 (the Snuggo), the Ergococoon and the Woombi address the problems of wrapping too loosely or too tightly since the degree of wrapping is predetermined by the suit.

As mentioned above, recent evidence shows that sucking on a pacifier is protective against SIDS. In addition, supplemental non-nutritive sucking (that is, sucking in addition to that required for feeding) is known to help to soothe an infant. Researchers have discovered that there is a clear reflex connection between the hand and mouth of a human fetus as early as 12-14 weeks after conception, and that thumb sucking in utero is common. After birth, many infants continue to soothe themselves by sucking on their thumbs or fingers. A newborn's ability to get the hands up to his or her mouth and suck is seen as a positive ability of the infant to organize him or herself in a self-soothing way. This helps establish an infant's ability to independently cope with stress and frustration.

Thus it would be an advantage to have a swaddle suit that overcomes the problems of improper swaddling and also provides an opportunity for non-nutritive sucking. This would improve the calming effect of the swaddling suit, since research that indicates that multiple simultaneous measures such as swaddling and sucking (along with rocking, white noise and other interventions) have an additive calming effect on crying infants: Karp H, Swaddling and excessive crying, Journal of Pediatrics, July 2007, e2. None of the aforementioned swaddling suits facilitates non-nutritive sucking.

None of WO 2007/098558 (the Snuggo), the Ergococcoon or the Woombi provide access to the hands while the infant is swaddled. Movement of the infant's arms in all three of these swaddling suits is restricted to 180 degrees below the shoulder line so the hands are restrained near the body but below the shoulder line, out of reach of the mouth.

U.S. Pat. No. 7,587,769 is a swaddling article including a blanket formed with opposed arm-receiving sleeves that attempts to facilitate non-nutritive sucking by securing a pacifier to the blanket, thus overcoming the problem of pacifiers falling out of an infant's mouth. The blanket incorporates a pacifier retaining structure to retain a pacifier relative to the blanket so that the pacifier is unable to fall away from the blanket. This keeps the pacifier positioned near the mouth when the blanket is wrapped around an infant so it is available for the infant to suck on at will. The pacifier retaining structure includes a flap of fabric secured to the upper edge of the swaddling blanket. The flap is drawn across the region of the baby's mouth.

A disadvantage of the swaddling article of U.S. Pat. No.7,587,769 is that it relies on a pacifier to be secured to the blanket. Another disadvantage is that it essentially extends the blanket across the face (around the mouth region), which can be uncomfortable and covering the face during sleep increases the risk of SIDs. Yet another disadvantage is that the swaddle article is in the form of a modified blanket and so lacks the convenience and advantages of a swaddling suit for example, the risk remains that the swaddle may loosen through movement thus becoming less effective and also posing a suffocation risk.

While research indicates that there are benefits associated with non-nutritive sucking (e.g. pacifier use), it also indicates that pacifier use may be associated with problems including:

interference with breast feeding, dependence on the pacifier (so the baby cannot sleep without one), an increased risk of middle ear infections, and dental problems associated with prolonged use.

Hence, despite the established benefits of pacifier use, many parents choose not to use pacifiers. Further, some infants simply do not take to pacifiers. In any event, so as to minimise interference with breastfeeding, the recommendation is to wait until nursing is going well (usually one month) before offering a pacifier. Thus pacifier use is not suitable for all infants and it would be an advantage to provide a means for non-nutritive sucking that does not rely on pacifier use.

Reflexes are set motor responses to specific sensory stimuli. Newborns have a hand-to-mouth reflex that is a natural instinct to get their hands to their mouths. Research indicates that this ability to access the hands for sucking is important for self-soothing. The hand-to-mouth reflex (along with the startle reflex) is one of a number of primitive reflexes present from birth or earlier. Primitive reflexes are thought to have provided evolutionary advantages to humans.

The somatosensory system is a complex system of receptors and processing centres that produce the senses including touch, motion perception (proprioception) and balance, and spatial perception of body parts (kinesthesia). The tactile or skin senses (that rely on skin sensors for touch and pressure) appear first during fetal development. The vestibular system, which is responsible for movement and balance perception, and the tactile (touch) sensors are highly developed in newborns.

The hand-to-mouth reflex goes with two reflexes that are considered essential to appropriate feeding responses in newborns: the rooting (or search) reflex and the sucking reflex. Both of these reflexes are triggered by a touch (including pressure) stimulus.

The rooting reflex occurs when the infant's cheek or corner of the mouth is touched or stroked. The infant's mouth opens to follow and "root" (search) in the direction of stroking or touch. Rooting helps the baby to become ready to suck. The suckling reflex is triggered by touching the mucous membranes on the inside of the mouth with any object. Both reflexes facilitate nursing.

In the hand-to-mouth reflex, when an infant's cheek is stroked, his or her mouth roots and the arm flexes. After hand and mouth find each other, the infant may suck energetically on the hands.

There is a need for a swaddling suit that does not suffer the disadvantages of a swaddling using a blanket and that effectively swaddles infants by sufficiently restraining movement of the limbs to suppress the startle reflex, yet still affords sufficient movement so that infants can get their hand(s) toward their mouth, so providing the opportunity for non-nutritive sucking without reliance on a pacifier.

U.S. Pat. No. 4,611,353 describes a swaddling garment in which an infant's arms are gently bound in a bent-elbow, hands-up position to inhibit the ability to fling open the arms without restricting arm movement. Binding of the arms in this manner is described as useful for holding a premature infant.

The BabySense Cuddlewrap is a blanket shaped to wrap an infant's arms tightly near to the body and face, again as a means for suppressing jerks of the arms and legs. However, neither the manufacturer of the BabySense Cuddlewrap nor the inventor of garment of U.S. Pat. No. 4,611,353 refer to the benefit of providing access to the hands for non-nutritive sucking while swaddled and neither swaddle addresses this need adequately.

While the swaddle of U.S. Pat. No. 4,611,353 is referred to as a garment, the part of the garment that is responsible for binding the arms in the manner described is two flaps of sufficient length to wrap around the infant and overlap each other, secured in place either by strips of hook and loop fasteners or simply by relying on the length of the flaps. Thus binding of the arms is achieved by a length of fabric in a manner analogous to a blanket. Loosening of the binding is possible with movement/wriggling of the baby—particularly in the embodiment that relies on the length of the flaps to secure the wrapping around the infant or where the hook and loop fastening is not sufficient to restrain loosening of the flaps through wriggling movement of the infant.

Therefore, the risks associated with use of swaddling blankets or cloths remain with both the BabySense Cuddlewrap and the swaddle of U.S. Pat. No. 4,611,353, including:

1. wrapping too tightly so as to suppress respiration;

2. overwrapping the infant in several layers of fabric so as to increase the risk of overheating (particularly as the preferred embodiment of U.S. Pat. No. 4,611,353 also includes a hood);

3. loosening of the swaddle around the upper body will result in excess fabric around the upper body, posing a suffocation risk to the infant;

4. the arms are only restrained so long as the swaddle remains tightly secured around the infant and loosening allows increasing movement of the arms;

5. the swaddle does not facilitate or maintain access to the hands, although access can initially be provided depending on how the hands are positioned when the infant is first swaddled.

Thus both U.S. Pat. No. 4,611,353 and the BabySense Cuddlewrap share many of the disadvantages of swaddling using a blanket, and do not act to secure the hands in position near the face to provide the opportunity for non-nutritive sucking without reliance on a pacifier.

It is an object of the present invention to provide a new or alternative swaddling suit that swaddles infants by restraining movement of the limbs and which overcomes the disadvantages of other swaddling suits by allowing movement of the hand towards the mouth and maintaining the hand in a position relative to the infant's face thereby facilitating non-nutritive sucking.

SUMMARY OF THE INVENTION

According to an aspect of the invention there is provided a swaddling suit for swaddling an infant, including:

(a) an upper portion for enclosing an infant's upper body, wherein the upper portion includes a bodice portion for enclosing an infant's torso and one or both arms, and wherein the bodice portion is configured to retain the infant's arm in a hand-raised position such that the hand is maintained in position relative to the infant's face;

(b) a lower portion including a pouch for enclosing the infant's legs; and (c) an opening to allow insertion of an infant into the swaddling suit, wherein the opening is closeable such that the swaddling suit is capable of being closed, the closed suit wrapping around the infant's body and limbs, thereby swaddling the infant therein, and wherein the swaddling suit restricts movement of the infant's limbs away from the body while allowing movement of the infant's hand towards the infant's mouth and maintaining the infant's hand in position relative to the infant's face, thereby facilitating non-nutritive sucking.

The invention thus provides a new or alternative swaddling suit and method for swaddling that swaddles infants by sufficiently restraining movement of the limbs to suppress the startle reflex, yet allowing movement of the hand towards the mouth and maintaining the hand in position relative to the infant's face thereby facilitating non-nutritive sucking.

For a better understanding of the invention and to show how it may be performed, a preferred embodiment will now be described, by way of non-limiting example only, with reference to the accompanying drawings and example.

FIGS. 1A and 1B show front and back views of a swaddling suit according to a preferred embodiment, with the back view shown in smaller scale than the front view. FIG. 1C shows the embodiment of FIG. 1A with an infant swaddled therein. FIG. 1A is a front view of a preferred embodiment.

FIG. 2A is a front view of a preferred embodiment.

FIG. 2B is a back view of a preferred embodiment.

FIG. 3A is a front view of an alternative embodiment.

FIG. 3B is a back view of an alternative embodiment.

Figures 5A, 5B:
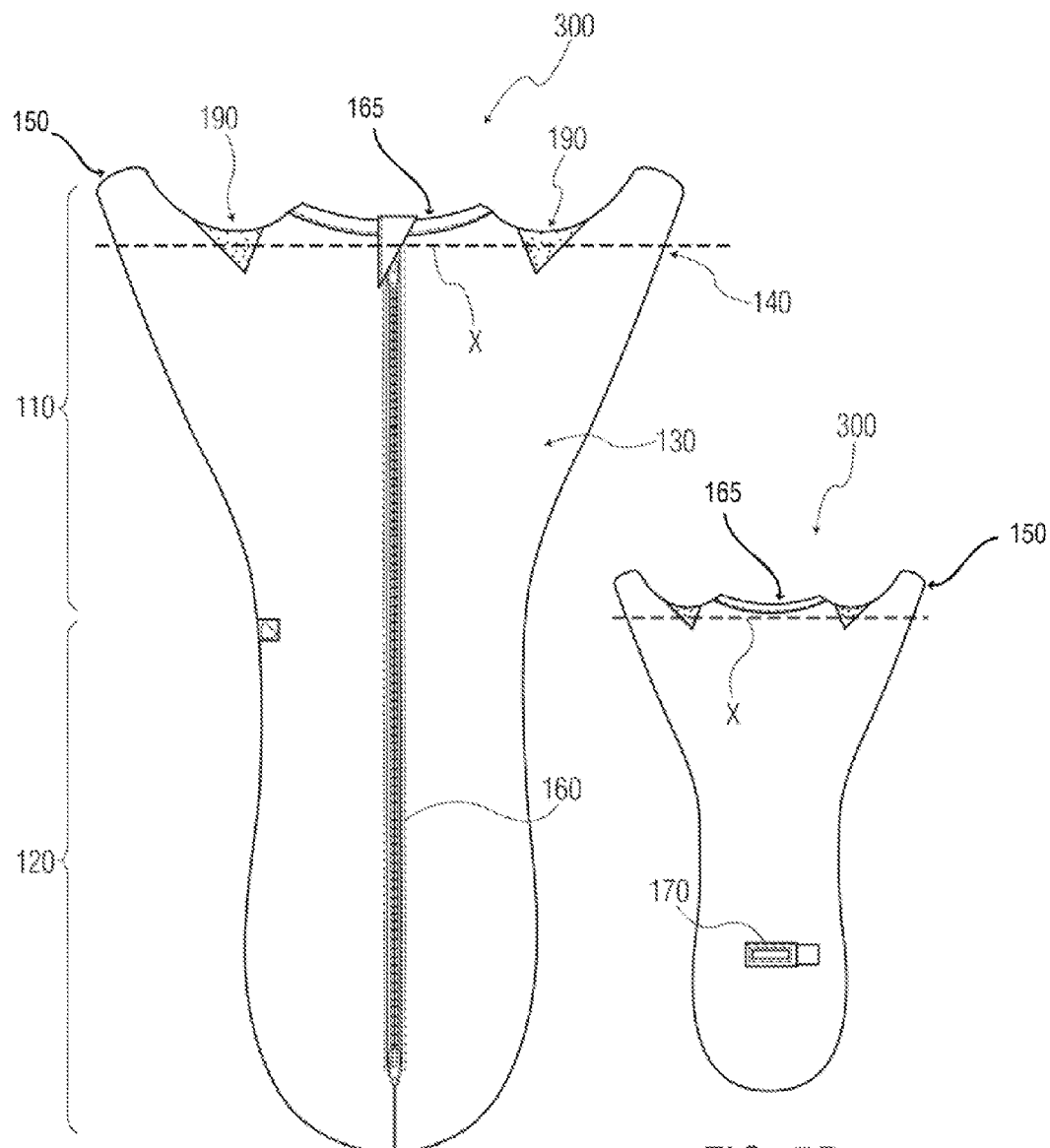
Figure 5C:
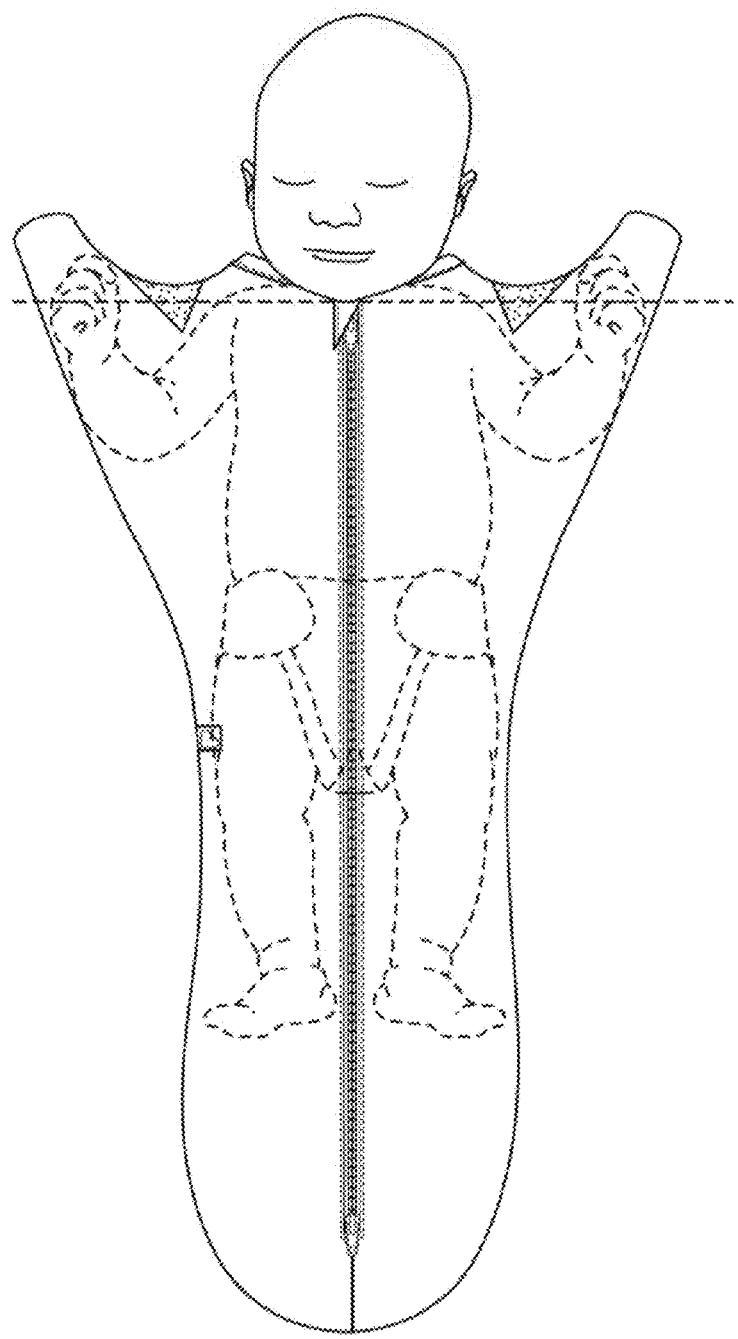
Figure 5D:
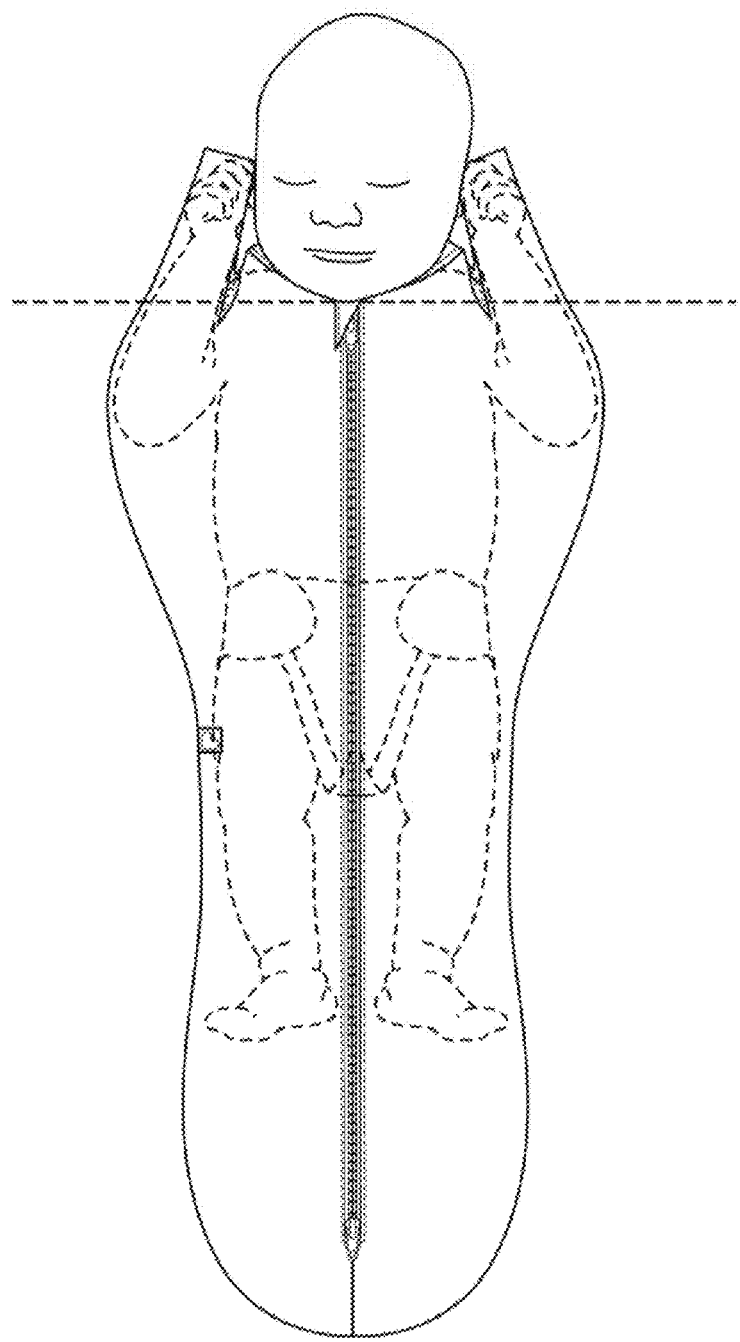
Figure 5E:
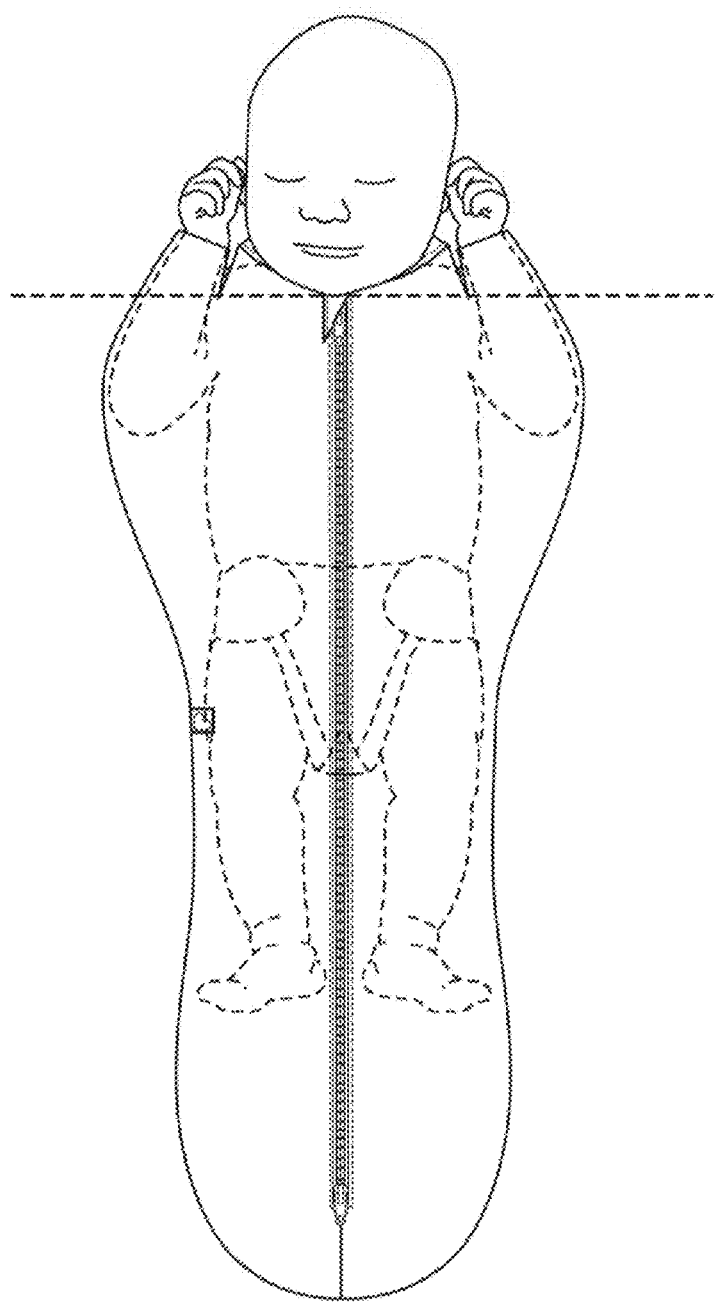

FIGS. 5A and 5B show front and back views of a swaddling suit according to yet another embodiment, with the back view shown in smaller scale than the front view. FIG. 5C shows the embodiment of FIG. 5A with an infant swaddled therein. FIG. 5C shows the embodiment of FIG. 5A with an infant swaddled therein. FIG. 5D shows the embodiment of FIG. 5C with an infant swaddled therein in another disposition. FIG. 5E shows a variation of the embodiment of FIG. 5D with an infant swaddled therein.

FIG. 5A is a front view of the embodiment.

FIG. 5B is a back view of the embodiment.

EXAMPLE 1 is a method of swaddling an infant.

DESCRIPTION OF PREFERRED EMBODIMENTS

The invention provides a new or alternative swaddling suit that swaddles infants by sufficiently restraining movement of the limbs to suppress the startle reflex, yet allowing movement of the hand towards the mouth and maintaining the hand in position relative to the infant's face thereby facilitating non-nutritive sucking and allowing the infant to self-soothe by sucking the hands. In this way, the swaddling suit offers advantages over other swaddling suits by providing greater protection against sudden infant death syndrome (SIDS) by virtue of facilitating non-nutritive sucking.

Infants swaddled in the swaddling suit can act on the hand-to-mouth reflex (the natural instinct to get their hands to their mouths) as the swaddling suit allows movement of the hands towards the mouth. Further, the swaddle suit maintains the infant's hand(s) in position relative to the face, improving access to the hands and increasing the opportunity for movement of the hands and/or arms, or the fabric of the swaddling suit itself, to trigger the rooting reflex. This is the natural instinct of the infant to search for something to suck on when the cheek is touched or stroked. In this way, the swaddling suit is designed to facilitate non-nutritive sucking—on the hand(s) or on the fabric of the swaddle suit near the hand(s).

Figures 1A, 1B:
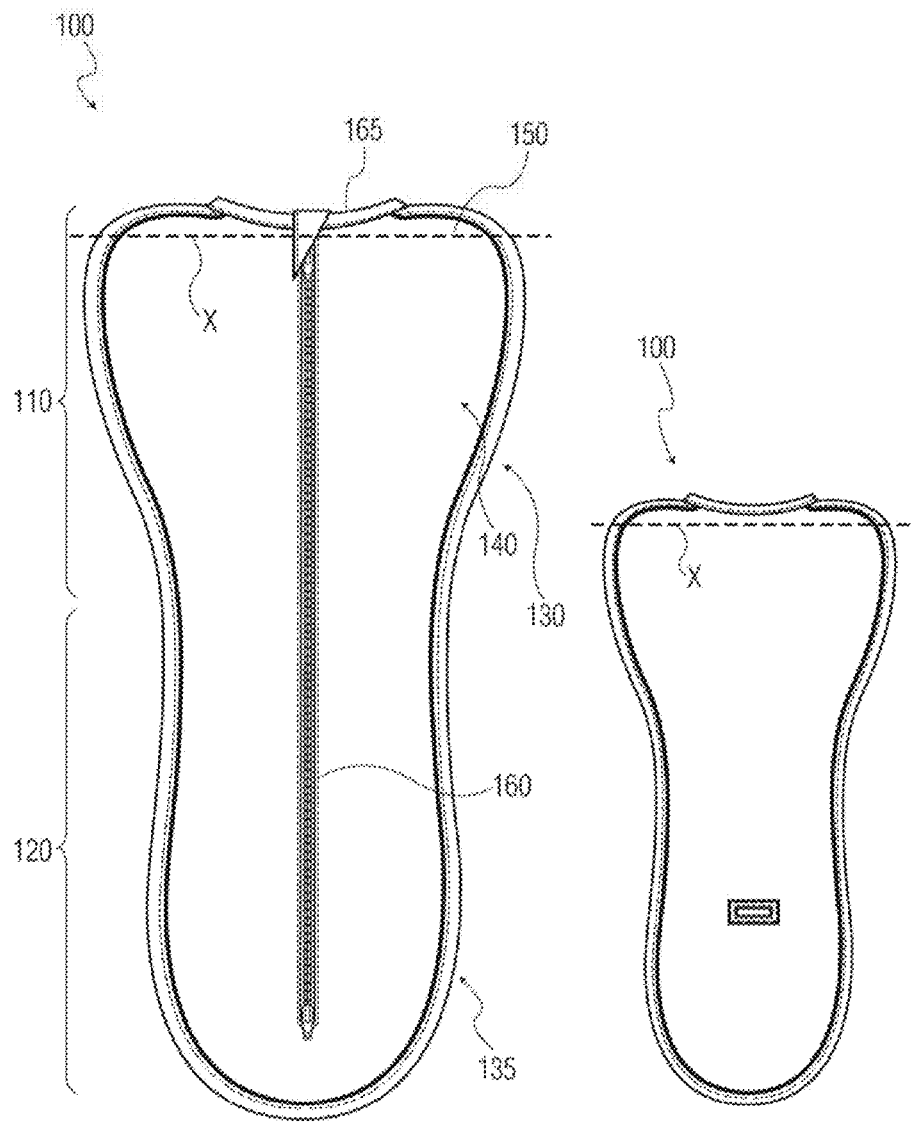
FIG. 1B is a back view of a preferred embodiment.

Referring to FIGS. 1A and 1B, front and back views are shown of a preferred embodiment of the swaddling suit 100 (see FIGS. 1A and 1B, respectively). The swaddling suit 100 includes:

1. an upper portion 110 for enclosing the infant's upper body; and
2. a lower portion 120 for enclosing the infant's lower body.

The upper portion 110 includes a bodice portion 130 for enclosing the infant's torso and arms. On each side of the bodice portion 130 is a wing portion 140 near the shoulder line of the suit 100. In this way, the wing portion 140 forms a T-like shape with the bodice portion 130 seen in FIGS. 1A and 1B as a rounded T-shape formed by the wing portions 140 extending laterally from the bodice portion 130 at the uppermost portion of the suit.

The wing portion 140 acts as a position-restricting means to maintain the hands in position relative to the face by virtue of the following:

1. each wing portion 140 is designed to receive one of the infant's arms in a hands-raised position, with the hands raised above the shoulder line—typically, with elbows bent and hands raised on both sides of the infant;
2. the wing portion 140 fits snugly around the arm thereby hugging the arm towards the infant's body in the aforementioned position thereby maintaining the hands up near the face; and
3. the wing portion 140 is shaped to taper in towards the infant's body under the bent elbow, thereby cupping the bent elbow and further assisting to support the hands up near the face and to restrict the infant from moving the hands away from the face, by preventing passage of the elbow out of the wing portion.

The wing portion 140 includes a wing tip 150 at its uppermost portion, to receive the infant's raised hand. The wing tip 150 assists to further secure the hand and retain it in place once in position. In one arrangement, the wing portion is resilient, the resilience further assisting to hug the arms towards the body and maintain the hand in position at the wing tip. The shape of the uppermost part of the upper portion also prevents the hands from travelling into the neck hole 165 (see inset, FIG. 3A), which can pose a choking risk to infants by restricting the neck hole 165.

In some arrangements, the wing portion 140 may include an internal pocket. The pocket may enclose the lower arm and hand, or just the hand in a glove-like fashion. This further assists in retaining the hand relative to the face.

The swaddling suit 100 facilitates non-nutritive sucking by the swaddled infant (and hence assists the infant to self-soothe by sucking the hands or the fabric of the swaddling suit near the hands) in the following ways:

1. the swaddling suit 100 makes the infant's hands accessible to the mouth by retaining the infant's hands in position relative to the face yet allowing the arms to move between adducted and abducted positions; and 2. the wing tip is configured so that it is able to brush or touch the infant's own cheek or the corner of his or her mouth when so moving the arm(s) and/or turning the head, thereby triggering the infant's rooting and/or hand-to-mouth reflexes.

By retaining the hand(s) near the mouth while allowing the infant to move the hand toward the mouth by adducting the arm and/or turning the head, the suit enables sucking of the hand(s) or fabric of the swaddling suit near the hands for self soothing (through non-nutritive sucking). Research has found that non-nutritive sucking is protective against SIDS. Known swaddling suits retain the hands away from the face by restricting movement of the hands to 180 degrees below the shoulder line. By restricting movement of the hand(s) to 180 degrees at or above the shoulder line, the swaddling suit 100 overcomes the problem of prior art swaddling suits that deny access of hands towards the mouth.

A further advantage of the T-like configuration of wing portions retaining the arms and hands in the hands-raised position on both sides of the infant is that the swaddled infant laid supine (on the back) for sleep is hindered from rolling over the arms into the prone (face down) position. This is further protective against the risk of SIDS.

Rolling is restricted by the positioning of the arms with elbows bent hands up above the shoulder line. However, if babies do manage to roll onto their front then they can use their arms to push up off the mattress, turn their head and keep breathing, minimising suffocation risk. Stronger babies have the advantage of being able to push themselves back to the supine position. Known swaddle garments bind the arms to the chest, preventing the infant from being able to use the arms to push up off the mattress.

The lower portion 120 of the swaddling suit 100 includes a pouch 135 for enclosing the infant's legs. The swaddling suit 100 tapers in at the waist line, below the wing portion 140. The suit 100 then widens to accommodate hip width and the lower portion 120 remains substantially the same width from around the hip down to the lowermost part (where the feet are enclosed). This is to ensure an even, snug fit of the swaddling suit 100 along the length of the infant.

The suit applies compressive pressure around the body, causing the suit 100 to hug the infant's contours. The compressive force assists to press the infant's arms towards the body. This provides resistance against full extension, thereby restricting movement of the infant's arms away from the body. In newborns, this wrapping of the infant's arms towards the body suppresses the full extensor startle response to loud noise or sudden movement. The startle response is the instinct of infants aged up to around 6 months to startle upon a loud noise or sudden movement, causing them to quickly spread out (extend) their limbs then draw (flex) them back in towards the body.

Thus the swaddling suit 100 confines the arms with hands above the shoulder line and near the face. The suit 100 also hugs the contours of the baby to further inhibit the startle response. The pressure applied by the swaddling suit 100 as it hugs the infant's contours also provides somatosensory (including proprioceptive) feedback to infants, assisting with infant's touch, movement and balance perception.

Figure 1C:
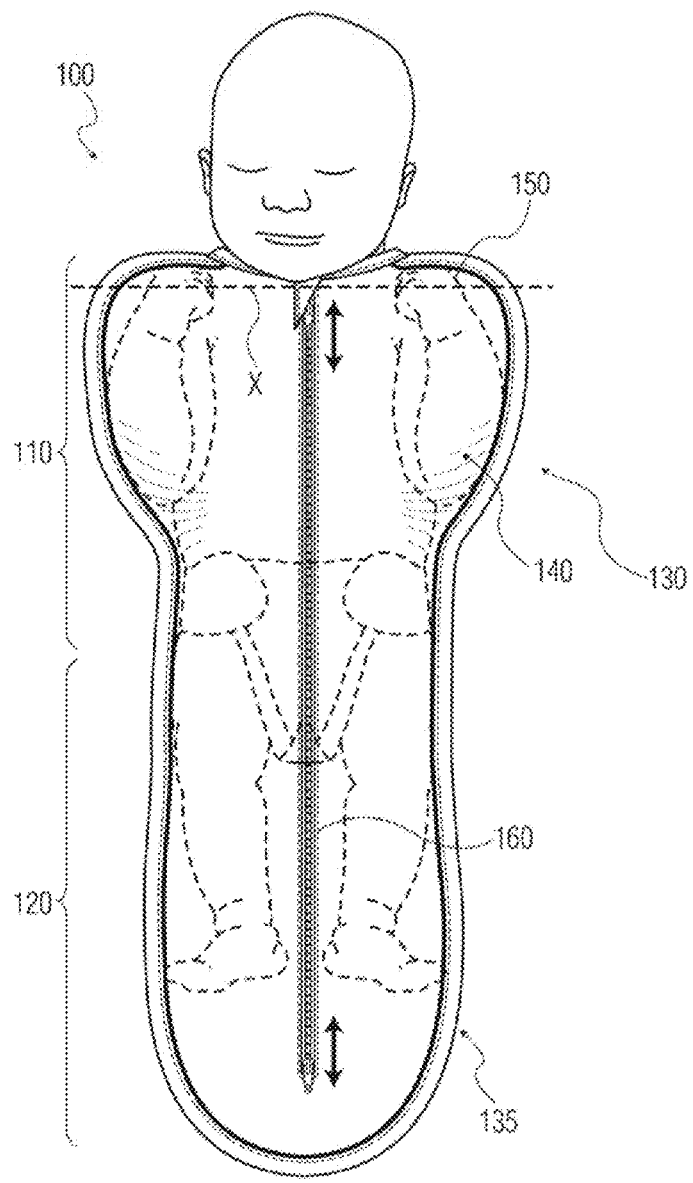

In one arrangement, the swaddling suit 100 shown in FIGS. 1A and 1B is made of a resilient material with two-way stretch (that is, resilience in both warp and weft directions). In one arrangement, the material is a fabric containing a percentage of elasticated yarn such as cotton spandex. However, the swaddling suit can be made using any suitable material for wrapping an infant, so long as the configuration of parts and shape of the wing portions secure the arms in a hands-up position with the hands positioned relative to the face such that the hands are accessible to the mouth as shown in FIG. 1C. The relative positioning of the hands to the mouth facilitates non-nutritive sucking and restricts movement of the arms and hands away from this position.

Extension of the limbs requires the infant to push against the compressive force applied by the suit 100 as it wraps around the infant. Where the suit 100 is made of resilient material, the resilience assists in tending the limbs towards the body by resisting full extension of the limbs while allowing the limbs to move between adducted and abducted positions (toward and away from the sagittal or longitudinal midline plane of the body). This further facilitates hand-to-mouth access by the infant. This is because the resilience further assists to maintain the hand relative to the face while permitting hand movement 180 degrees below the shoulder (the approximate position of the shoulder line is demarcated by the dashed line marked X in FIGS. 1, 2, 4 and 5).

The swaddling suit 100 has an opening 160 to allow insertion of an infant into the suit. The opening 160 is closeable by any suitable closure means, including hook and loop fasteners, zipper means, buttons or any other method of fastening the opposing sides of the opening together. In the preferred embodiment, the opening 160 extends longitudinally along the swaddling suit 100, from the upper portion to the lower portion (see FIG. 1A). However, in some arrangements, the opening 160 may be shorter than is illustrated or be positioned elsewhere such as along a side seam or running along the lowermost seam of the lower portion 120.

In a preferred embodiment, the closure means is a two-way zipper extending along the opening, allowing the opening 160 to be partially openable from either end. Any other closure means (e.g. buttons, press studs) that allows partial opening from either end can also be used. When opened from the lower portion end, the opening 160 provides access to the infant's lower body (e.g. for changing nappies or using a child restraint in a car or pram) while the upper body remains swaddled. Alternatively, the closure means does not provide two-way access (not illustrated) but the opening is positioned such that access to the lower body is possible while the upper body remains swaddled (e.g. by positioning the opening with closure means along a seam).

In a preferred embodiment, the swaddling suit 100 comprises a front panel (FIG. 1A) secured to a back panel (FIG. 1B). The front panel is configured to cover the front of an infant enclosed within the suit, and the back panel is configured to cover the back of the infant. In some arrangements, the upper portion and lower portion are continuous, formed by front and back panels that extend the full length of the swaddling suit 100—as illustrated. In other arrangements, the front and/or back panels comprise adjoining subpanels that collectively extend the full length of the swaddling suit (not illustrated).

In the preferred embodiment, the opening 160 is positioned on the front panel of the swaddling suit 100 for example, as shown in FIG. 1A, extending lengthways along the centre of the front panel from the neck hole 165 to the lower portion of the suit 100. The opening can also be positioned off-centre or along a side seam.

Referring to FIG. 1B, a slot 170 allows passage of a child restraint belt (e.g. car seatbelt) through the suit 100. The slot 170 enables the belt to pass through the internal volume and exit through a corresponding portion of the opening 160. As the opening 160 can be partially opened, it can remain substantially closed while allowing the belt passage through the suit. This allows the infant to be secured for transportation while remaining swaddled.

Figures 2A, 2B:
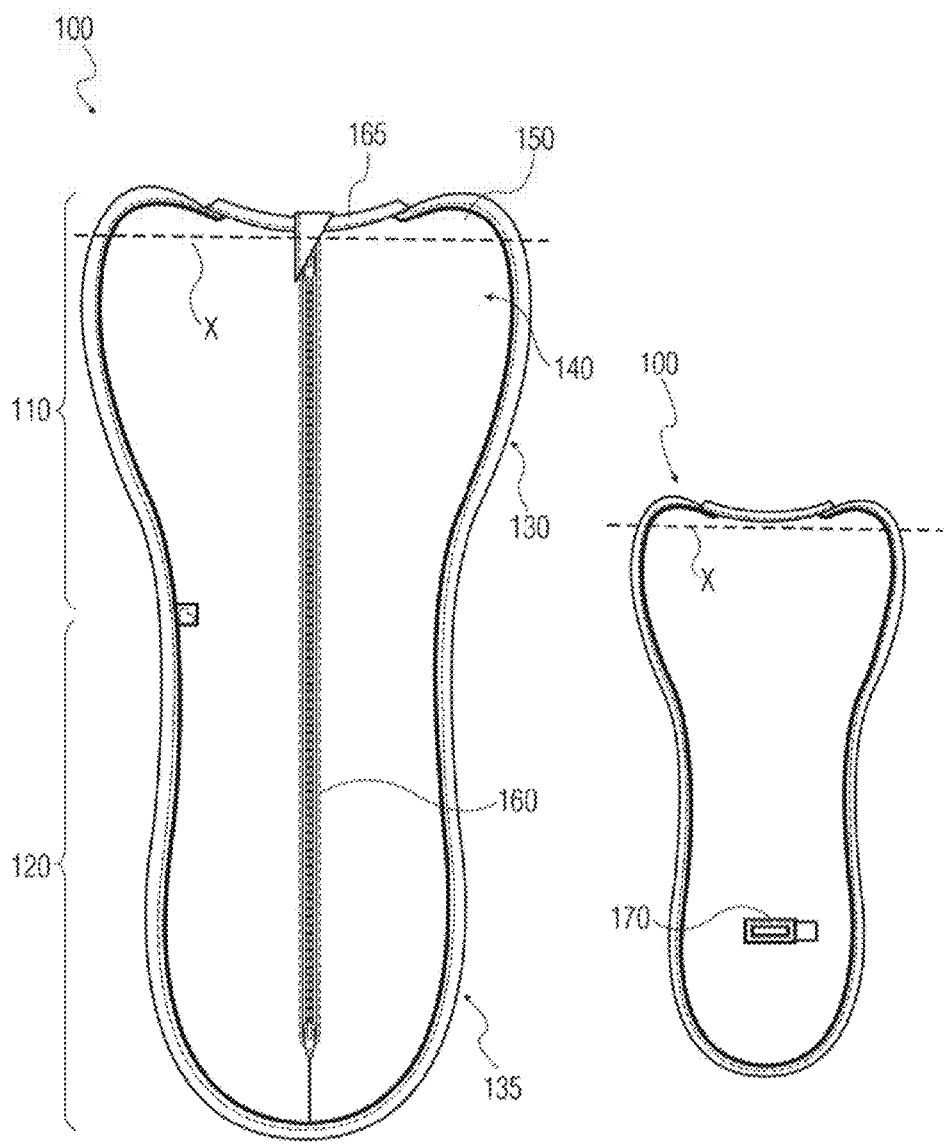
FIGS. 2A and 2b show front and back views of an alternative arrangement of the embodiment shown in FIGS. 1A and 1B, with the back view shown in smaller scale than the front view.

Referring to FIGS. 2A and 2B, an alternative arrangement of the embodiment illustrated in FIGS. 1A and 1B is shown, in which the swaddling suit 100 has wing tips 150 that clearly extend above the shoulder line (the approximate position of the shoulder line is demarcated by the dashed line labeled X in FIGS. 2A and 2b). It can be seen by comparing FIGS. 1 and 2 that the wing tip 150 (i.e. the uppermost portion of the wing portion 140) may be shaped to accommodate the hands substantially at or near the shoulder line (FIGS. 1A and 1B) or above the shoulder line (FIGS. 2A and 2B). The embodiment of FIGS. 2A and 2B otherwise retains the same features as the embodiment depicted in FIGS. 1A and 1B.

Figures 3A, 3B:
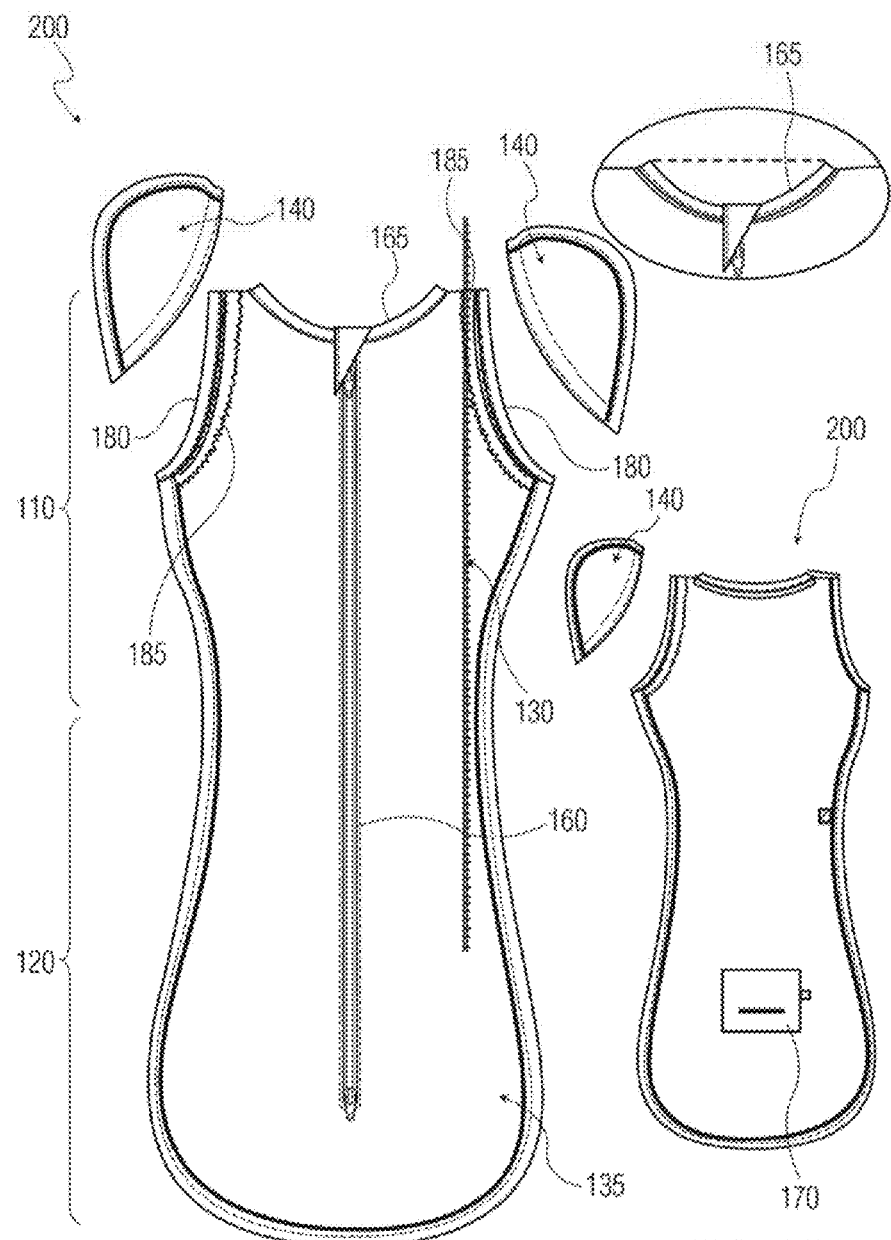
FIGS. 3A and 3B show front and back views of a swaddling suit according to an alternative embodiment, with the back view in smaller scale than the front view.
Figure 4A:
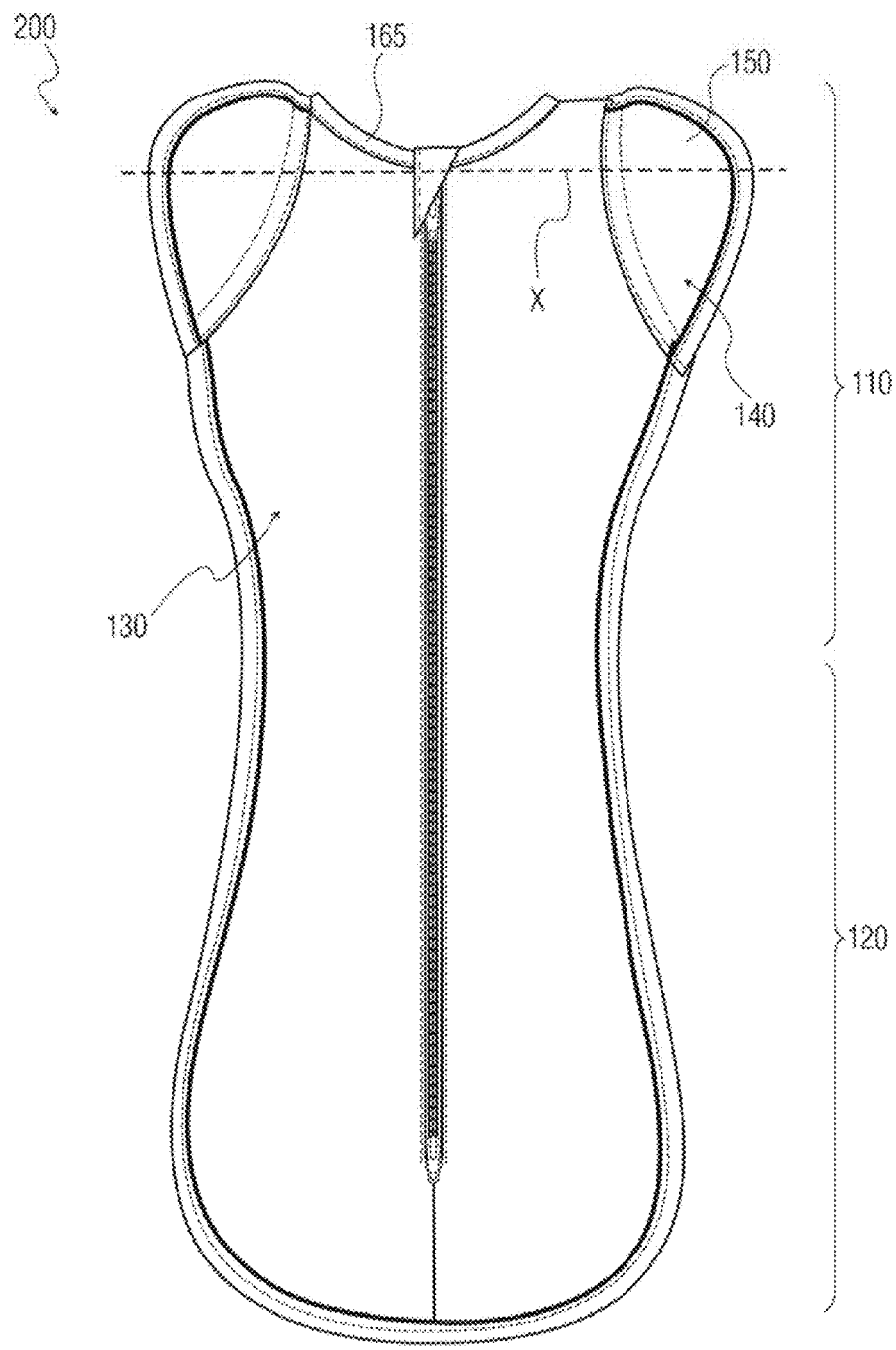
FIG. 4A shows a front view of the embodiment of FIG. 3A, showing the detachable wing portions attached.
Figure 4B:
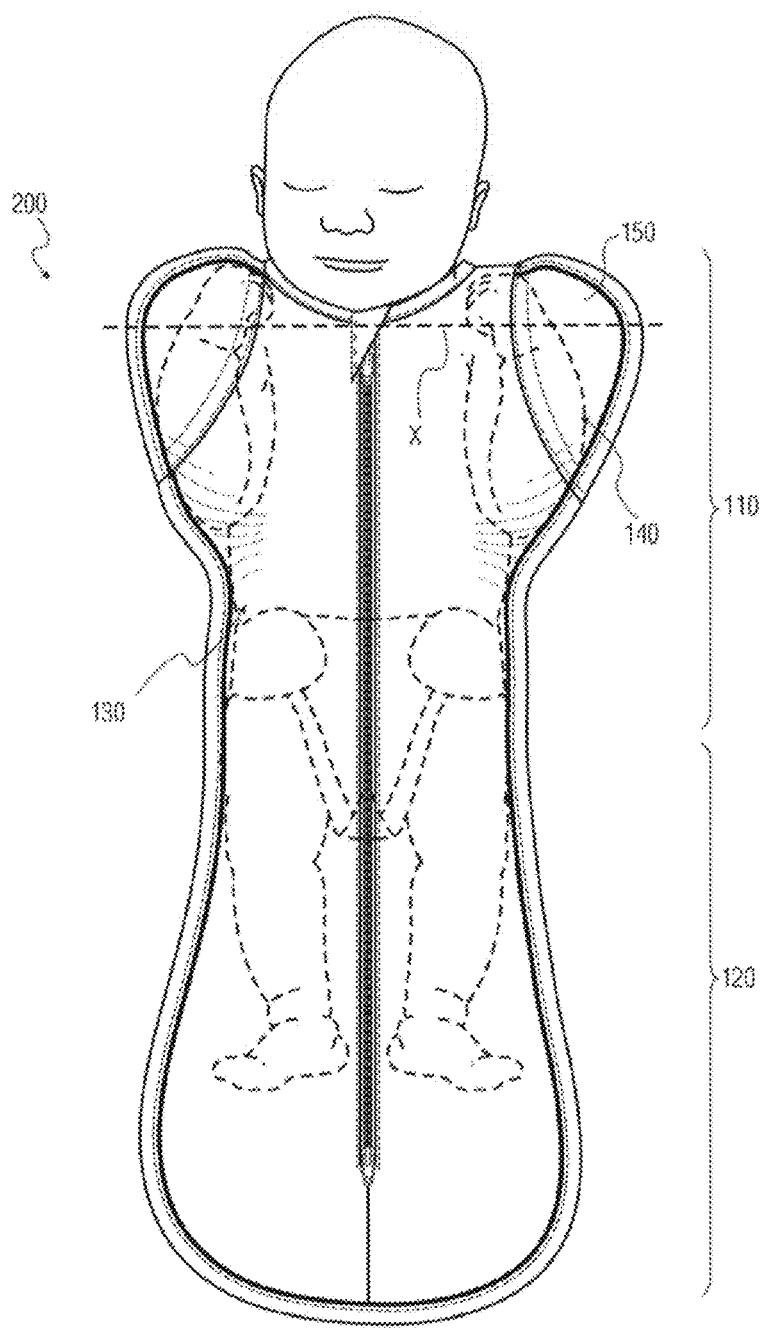
FIG. 4B shows the embodiment of FIG. 4A with an infant swaddled therein.

Referring to FIGS. 3A and B and 4A and B, an alternative embodiment 200 is shown in which each wing portion 140 is detachable from the bodice portion 130. FIGS. 3A and 3B shows the wing portions 140 detached while FIG. 4 shows the wing portions 140 attached. The detachable wing portions 140 can be fastened to the bodice portion using any suitable fastening means, such as the hook and loop fasteners shown in FIGS. 3A and 3B labeled item 185 or a zipper means.

Removal of the wing portions 140 leaves an armhole 180 on either side of the bodice portion 130 (see FIGS. 3A and 3B). An infant wearing the swaddling suit 100 is able to become unswaddled by extending the arms completely out from the suit through the armholes 180. This embodiment 200 assists parents to transition the infant out of swaddling by removing a first wing portion 140 and leaving the second wing portion attached so that one of the infant's arms is still maintained in the elbows-bent-and-hands-raised position. The swaddling suit 200 is used in this manner for a transition period (e.g. a few weeks) to allow the infant to accommodate to having one arm completely out and free to move. The next step is to remove the second wing portion, in which case the infant is no longer swaddled and the suit 200 acts like a sleeping bag.

In the embodiment 200 shown in FIGS. 3 and 4, the lower portion 120 is shaped so that it is wider at its lowermost end than around the waist. This is in contrast to the embodiment 100 of FIGS. 1 and 2, in which the lower portion tapers in below the wing portion then expands to accommodate the hip and then remains substantially the same width down to the feet. The shape of the lower portion 120 of the embodiment 200 of FIGS. 3 and 4 allows a greater degree of freedom of movement of the lower limbs than the first embodiment, which reflects use of this embodiment 200 in infants being prepared for transition out of swaddling. The embodiment 200 of FIGS. 3 and 4 otherwise retains the same features of the embodiment 100 described in relation to FIGS. 1 and 2. Items bearing the same item label in different figures depict the same feature in different arrangements/embodiments.

Referring to FIGS. 5A and 5B, a third embodiment 300 is shown, in which the position-restricting means that retains the hands near the face includes:

1. wing portions 140 configured to receive the arms in a hand-raised position, with the hands raised above the shoulder line; and 2. a tension pouch 190 intermediate each wing portion 140 and the bodice portion 130.

In this embodiment 300, as can be seen in FIGS. 5C and D, the wing portions 140 act like sleeves to receive the lower arms. The ends of the wing portions 140 may be open, allowing the hands to extend through the open end as shown in FIG. 5E. Alternatively, the ends of the wing portions 140 may be closed so that the hands are retained within the wing portions 140 as shown in FIGS. 5C and D. In contrast to the embodiments 100 and 200 of FIGS. 1 to 4, the embodiment 300 of FIGS. 5A-D relies on tension to resist the hands moving away from the face, rather than pressure to tend the hands toward the face. When the wing portions 140 are open, the arms may extend up through the wing portion resulting in the elbow being extended away from the bent position. However, the hand is still retained in position relative to the face and accessible to the mouth by virtue of the tension pouch 190. The tension pouch 190 biases the infant's arm toward the elbow-bent-and-hand-raised position such that the hand is retained in a position relative to the face and the infant is able to move the hand towards the mouth as can be seen in FIGS. 5D and 5E. The embodiment of FIGS. 5A and 5B otherwise retains the same features as the embodiment depicted in FIGS. 1A and 1B.

Method of Swaddling an Infant

The invention also provides a new or alternative method of swaddling an infant using a swaddling suit that improves protection against SIDS by facilitating non-nutritive sucking.

A specific example is provided below.

EXAMPLE 1

The example relies on a swaddling suit that retains the hands near the face and that sufficiently restricts movement of the limbs to suppress the startle reflex, while allowing baby movement of hand to mouth.

Using the embodiment 100 illustrated in FIGS. 1A and B:

1. Insert an infant's legs through the opening of the swaddling suit, so that the legs are received by the pouch;

2. Insert the infant's torso and arms through the opening into the upper portion of the swaddling suit;

3. Insert the arms up into the wing portions;

4. Tuck the hands into the wing tip;

5. Close the opening of the suit by closing the closure means.

An advantage of any of the preferred embodiments is that the swaddling suit swaddles infants by sufficiently restraining movement of the limbs to suppress the startle reflex, yet allowing movement of the hand towards the mouth and maintaining the hand in position relative to the infant's face such that the hands are accessible to the mouth. The relative positioning of the hands to the mouth facilitates non-nutritive sucking and restricts movement of the arms and hands away from this position. In this way, the swaddling suit offers advantages over other swaddling suits by providing greater protection against sudden infant death syndrome (SIDS) by virtue of facilitating non-nutritive sucking in combination with the advantages of swaddling.

A further advantage of the preferred embodiments is that the swaddling suit facilitates non-nutritive sucking without relying on a pacifier.

Yet another advantage of the swaddling suit is that the arms are semi-restrained in a position that reduces the risk of the swaddled infant rolling over into the prone position from the supine position. If the infant does roll onto his or her front, the hands are positioned so they are available to the infant (rather than being bound to the body) to push him- or herself up at least so the infant can lift the head and turn it to the side, or even to push him- or herself back into a supine position, thereby minimising the risk of suffocation. This is further protective against the risk of SIDS.

The invention provides a swaddling suit for use in swaddling infants and which assists to protect against SIDS by facilitating non-nutritive sucking in combination with the advantages of swaddling. The swaddling suit has been developed primarily for use as a means for swaddling infants for safe sleeping. However, it will be appreciated that the invention is not restricted to these particular fields of use and that it is not limited to particular embodiments or applications described herein.

The invention claimed is:

1. A swaddling suit for swaddling an infant comprising,
an upper portion for enclosing the infant's upper body, wherein the upper portion includes
(a) a bodice portion, and
(b) one wing portion of the swaddling suit on one side of the
(c) wing portions comprising one wing portion of the swaddling portion on another side of the bodice portion and another wing portion of the swaddling portion on another side of the bodice portion, said one wing portion and said another wing portion extending laterally from the bodice portion at an uppermost portion of the suit,
each of said one wing portion and said another wing portion having a wing tip at an uppermost portion of each of the wing portions that is positioned above a level of the neck hole of said suit,
each of said wing portions being large enough to completely surround and retain an infant's arm and hand in a hand-raised and elbow-bent position,
said swaddling suit being tapered in at a waist line below said wing portions and then widening whereby a narrowest region of said suit is at said waist line.

2. A swaddling suit for swaddling an infant, said swaddling suit being formed by a front panel secured to a back panel, said swaddling suit further including:
an upper portion for enclosing the infant's upper body and one or both arms, wherein the upper portion includes:
(a) a bodice portion for enclosing an infant's torso;
(b) a neck hole at an uppermost central portion of the bodice portion, and
(c) a wing portion on each side of the bodice portion, each wing portion extending laterally from the bodice portion at an uppermost portion of the suit and having a wing tip at an uppermost portion of the wing portion that is positioned above a level of the neck hole of said suit,
each wing portion being large enough to completely surround and retain an infant's arm,
said swaddling suit being tapered in at a waist line below each wing portion and then widening whereby a narrowest region of said suit is at said waist line.

3. A swaddling suit according to claim 1 or 2 wherein a width of the suit between the wing portions is greater than a width of the bodice portion.

4. A swaddling suit according to claim 1 or 2 wherein a shape of the suit is rounded to follow the contours of the infant.

5. A swaddling suit according to claim 1 or 2 wherein the suit comprises a front panel secured to a back panel,
wherein the front panel is configured so that it is able to cover the front of an infant enclosed within the suit, and
wherein the back panel is configured so that it is able to cover the back of an infant so enclosed.

6. A swaddling suit according to claim 5 wherein the back panel includes a slot, wherein the slot is configured to allow passage of a child restraint belt.

7. A swaddling suit according to claim 1 or 2 wherein said swaddling suit comprises a material which includes elasticated yarn.

8. A method for swaddling an infant including the steps of:
(a) inserting an infant's upper body into an upper portion of a swaddling suit according to claim 1 or 2; and
(b) inserting the infant's arm into a wing portion of said swaddling suit.

9. A method for swaddling an infant according to claim 8 including a further step of tucking each of the infant's hands into a wing tip of said swaddling suit.

10. A method for swaddling an infant according to claim 8 including a further step of inserting an infant's legs into a lower portion of said swaddling suit.

11. A method for swaddling an infant according to claim 8 including a final step of closing the swaddling suit, the closed suit forming a fitted garment to swaddle the infant therein.

12. A swaddling suit according to claim 1 or 2 wherein the suit further includes a lower portion for enclosing the infant's lower body.

13. A swaddling suit according to claim 12 wherein the swaddling suit has an opening to allow insertion of an infant into the suit, said swaddling suit further comprising a closure for closing said suit to swaddle the infant therein.

14. A swaddling suit according to claim 13 wherein the closure means is a zipper.

15. A swaddling suit according to claim 12 wherein the upper portion and a lower portion of the swaddling suit are continuous.

16. A swaddling suit according to claim 1 or 2 wherein the suit acts as a fitted garment swaddling an infant in a single layer of material.

17. A swaddling suit according to claim 1 wherein said swaddling suit is made of a material that is resilient.

18. A swaddling suit according to claim 17 wherein said swaddling suit is made of a material that is resilient in warp and weft directions.

* * * * *

UNITED STATES PATENT AND TRADEMARK OFFICE
CERTIFICATE OF CORRECTION

PATENT NO. : 9,179,711 B2
APPLICATION NO. : 12/920034
DATED : November 10, 2015
INVENTOR(S) : Krawchuk It is certified that error appears in the above-identified patent and that said Letters Patent is hereby corrected as shown below:

IN THE CLAIMS

In claim 1, at column 11, line 18, replace

"(b) one wing portion of the swaddling suit on one side of the (c) wing portions comprising one wing portion of the swaddling portion on another side of the bodice portion and another wing portion of the swaddling portion on another side of the bodice portion, said one wing portion and said another wing portion extending laterally from the bodice portion at an uppermost portion of the suit,"

with

--(b) a neck hole at an uppermost central portion of the bodice portion, and (c) wing portions comprising one wing portion of the swaddling suit on one side of the bodice portion and another wing portion of the swaddling portion on another side of the bodice portion, said one wing portion and said another wing portion extending laterally from the bodice portion at an uppermost portion of the suit,--.

Signed and Sealed this
Second Day of February, 2016

Michelle K. Lee
*Director of the United States Patent and Trademark Office*

(12) INTER PARTES REVIEW CERTIFICATE (3444th)
United States Patent
Krawchuk

(10) Number: US 9,179,711 K1
(45) Certificate Issued: Feb. 9, 2024

(54) SWADDLING SUIT

(75) Inventor: Hana-Lia Krawchuk

(73) Assignee: BIG BEINGS USA PTY LTD

Trial Number:

IPR2020-01234 filed Jul. 2, 2020

Inter Partes Review Certificate for:

Patent No.: 9,179,711
Issued: Nov. 10, 2015
Appl. No.: 12/920,034
Filed: Aug. 27, 2010

The results of IPR2020-01234 are reflected in this inter partes review certificate under 35 U.S.C. 318(b).

INTER PARTES REVIEW CERTIFICATE
U.S. Patent 9,179,711 K1
Trial No. IPR2020-01234
Certificate Issued Feb. 9, 2024

AS A RESULT OF THE INTER PARTES REVIEW PROCEEDING, IT HAS BEEN DETERMINED THAT:

Claims 1, 17 and 18 are found patentable.

Claims 2-16 are cancelled.

\* \* \* \* \*